US008380446B2

(12) United States Patent  
Mostowfi et al.

(10) Patent No.: US 8,380,446 B2  
(45) Date of Patent: Feb. 19, 2013

(54) SYSTEM AND METHOD FOR DETERMINING THE PHASE ENVELOPE OF A GAS CONDENSATE

(75) Inventors: Farshid Mostowfi, Edmonton (CA); Anil Singh, Edmonton (CA); John Ratulowski, Edmonton (CA)

(73) Assignee: Schlumberger Technology Corporation, Sugar Land, TX (US)

(*) Notice: Subject to any disclaimer, the term of this patent is extended or adjusted under 35 U.S.C. 154(b) by 197 days.

(21) Appl. No.: 12/815,304

(22) Filed: Jun. 14, 2010

(65) Prior Publication Data

US 2011/0307186 A1  Dec. 15, 2011

(51) Int. Cl.  
  *G01N 31/00* (2006.01)  
  *G01N 7/00* (2006.01)

(52) U.S. Cl. .......................... 702/24; 73/29.01

(58) Field of Classification Search .......... 702/24, 702/50, 81, 84, 98–100, 127, 131, 138, 189–190; 73/1.06, 1.57, 19.05, 19.12, 23.2, 23.27, 73/24.04, 25.04, 29.01, 29.03, 30.02, 31.04, 73/61.41, 61.43–61.44, 61.47, 61.62, 61.78, 73/64.45–64.46; 137/1–3, 7, 12, 14; 210/97, 210/110, 130, 133, 150–151, 739, 741–742; 422/68.1, 81, 82.12–82.13, 83, 502, 504–505, 422/507, 527  
See application file for complete search history.

(56) References Cited

U.S. PATENT DOCUMENTS

| 6,428,666 B1 | 8/2002 | Singh et al. |
| 6,543,274 B1 | 4/2003 | Herrmann et al. |
| 2002/0098122 A1 | 7/2002 | Singh et al. |
| 2004/0098202 A1 | 5/2004 | McNeil, III et al. |
| 2006/0008382 A1 | 1/2006 | Salamitou et al. |
| 2006/0008913 A1 | 1/2006 | Angelescu et al. |

FOREIGN PATENT DOCUMENTS

| AU | WO0201211 A1 | 1/2002 |
| CA | WO2009109868 A1 | 9/2009 |
| DE | 10035527 A1 | 1/2002 |
| FR | 2804508 | 8/2001 |

(Continued)

OTHER PUBLICATIONS

Angelescu et al., Highly Integrated Microfluidic Sensor, 2008, Proc. of SPIE, vol. 6886, 9 pp.*

(Continued)

*Primary Examiner* — Toan Le  
(74) *Attorney, Agent, or Firm* — Daren C. Davis; Wayne I. Kanak

(57) ABSTRACT

A system for determining the phase envelope of a gas condensate includes a microfluidic device defining an entrance passageway, an exit passageway, and a microchannel in fluid communication with the passageways. The system includes an input sample bottle in fluid communication with the entrance passageway and a first pump associated with the input sample bottle for urging the gas condensate, in the input sample bottle, into the entrance passageway. The system further includes an output sample bottle in fluid communication with the exit passageway and a second pump associated with the output sample bottle for pressurizing the gas condensate, in the output sample bottle, into the exit passageway in opposition to the first pump. The system includes a temperature control device for controlling the temperature of the gas condensate in the microchannel. The first pump and the second pump operate to provide a desired pressure drop across the microchannel.

24 Claims, 5 Drawing Sheets

FOREIGN PATENT DOCUMENTS

| | | |
|---|---|---|
| RU | EP1677100 B1 | 9/2003 |
| US | 0542582 A1 | 5/1993 |

OTHER PUBLICATIONS

Tsai et al., Active Microfluidic Mixer and Gas Bubble Filter Driven by Thermal Bubble Micropump, 2002, Sensors and Actuators A 97-98, pp. 665-671.*

Hartman et al., Distillation in Microchemical Systems Using Capillary Forces and Segmented Flow, Apr. 7, 2009, Lab on a Chip, pp. 1843-1849.*

Bowden et al, The liquid—liquid diffusive extraction of hydrocarbons from a North Sea oil using a microfluidic format, The Royal Society of Chemistry, 2006, 6, 740-743, first published as an Advance Article on the web Apr. 13, 2006.

Dong Sung Kim et al, A Serpentine Laminating Micromixer Combining Splitting/recombination and Advection. The Royal Society of Chemistry 2005, 5, 739-747, First published as an Advance Article on the web Apr. 26, 2005.

Mark E. Steinke, et al. Single-Phase Heat Transfer Enhancement Techniques in Microchannel and Minichannel Flows, Thermal analysis and Microfluidics Laboratory, Mechanical Engiineering Department, rochester Institute of Tecchnology, Rochester, NY, USA, Jun. 17-19, 2004, p. 141-148.

Elisabeth Verpoorte et al, Microfluidics Meets MEMS, Proceedings of the IEEE, vol. 91, No. 6, Jun. 2003, p. 930-953.

D. Jed Harrison et al, Micromachining a Miniaturized capillary Electrophoresis-Based Chemical analysis System on a Chip, Science, New Series, vol. 261, No. 5123. (Aug. 13, 1993), pp. 895-397.

Chih-Jung Kuo, et al, Bubble Dynamics During Boiling in Enhanced Surface Microchannels, Journal of Microelectromechanical Systems, vol. 15, No. 6 Dec. 2006, pp. 1514-1527.

International Search Report and Written Opinion of PCT Application No. PCT/IB2011/052478 dated Oct. 7, 2011.

Xiong et al., "Flow characteristics of water in straight and serpentine micro-channels with miter bends," Experimental Thermal and Fluid Science, 2007, vol. 31: pp. 805-812.

\* cited by examiner

SYSTEM AND METHOD FOR DETERMINING THE PHASE ENVELOPE OF A GAS CONDENSATE

BACKGROUND OF THE INVENTION

1. Field of the Invention

The present invention relates to a system and method for determining the phase envelope of a gas condensate.

2. Description of Related Art

Phase behavior studies of lean gas condensates are of growing importance in petroleum reservoir analysis. The dropout of condensate near a wellbore can significantly limit the recovery efficiency of hydrocarbons from the reservoir. Moreover, condensate yield at the surface of a well is a key parameter for determining the size of a liquid management system at the well. The dew point of a gas condensate is one of the most important thermo-physical properties of such fluids. However, the measurement of the dew point of a gas condensate is typically difficult to perform in conventional pressure-volume-temperature (PVT) systems. In such conventional systems, the subject fluid is injected into a pressure-balanced glass chamber. The dew point is detected by visually observing the formation of mist in the chamber as the pressure and temperature of the fluid are closely monitored. While improvements have been made to this basic PVT system, challenges stem from the difficulty in detecting and quantifying very small volumes of liquid in the gas. For example, dew point measurements become increasingly difficult as the liquid content of a gas decreases and other problems, such as liquid holdup on the chamber walls, occur. Conventional methods using PVT cells become challenged when measuring the dew point of fluids with less than about 1-2 percent liquid content by volume. Furthermore, conventional techniques often suffer from poor repeatability, poor reproducibility, and poor accuracy.

There are devices and methods for making measurements related to determining the phase envelope of a gas condensate that are well known in the art, however, considerable shortcomings remain.

BRIEF SUMMARY OF THE INVENTION

In one aspect, the present invention provides a system for determining the phase envelope of a gas condensate. The system comprises a microfluidic device defining an entrance passageway, an exit passageway, and a microchannel in fluid communication with the entrance passageway and the exit passageway. The system further comprises an input sample bottle in fluid communication with the entrance of the microfluidic device and a first pump operably associated with the input sample bottle for urging the gas condensate, disposed in the input sample bottle, into the entrance of the microfluidic device. The system further comprises an output sample bottle in fluid communication with the exit of the microfluidic device and a second pump operably associated with the output sample bottle for controlling the pressure of the gas condensate, disposed in the output sample bottle, in opposition to the first pump. The first pump and the second pump are operable to provide a desired pressure drop across the microchannel of the microfluidic device. The system yet further comprises a temperature control device to control the temperature of the gas condensate in the microchannel.

In another aspect, the present invention provides a method for determining the phase envelope of a gas condensate. The method comprises injecting a gas condensate into a microchannel of a microfluidic device at a pressure above the expected dew point of the gas condensate and monitoring the gas condensate in the microchannel for an indication of a phase change of the gas condensate.

The present invention provides significant advantages, including (1) providing a way to measure the dew point of a gas condensate in much less time than required by conventional techniques; (2) providing a way to measure the dew point of a gas condensate that is much less labor intensive than by conventional techniques; and (3) providing a way to measure the dew point of a flammable gas condensate that is safer than by conventional techniques, as much less gas condensate is required.

Additional objectives, features and advantages will be apparent in the written description which follows.

BRIEF DESCRIPTION OF THE DRAWINGS

The novel features characteristic of the invention are set forth in the appended claims. However, the invention itself, as well as a preferred mode of use, and further objectives and advantages thereof, will best be understood by reference to the following detailed description when read in conjunction with the accompanying drawings, in which the leftmost significant digit(s) in the reference numerals denote(s) the first figure in which the respective reference numerals appear, wherein:

Figure 1:
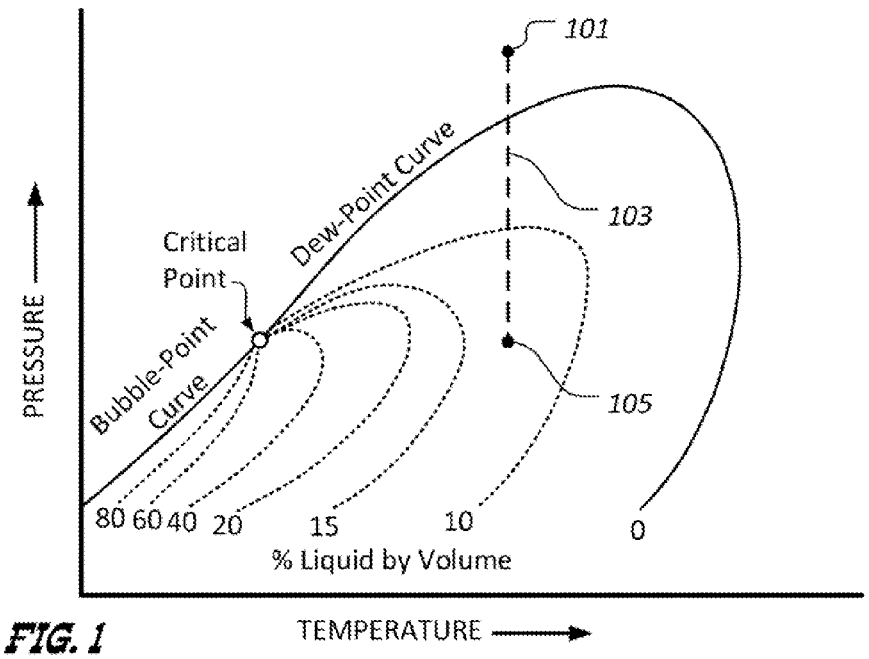
FIG. 1 is a graphical representation of the phase behavior of one particular, typical, gas condensate.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the scope of the invention as defined by the appended claims.

DETAILED DESCRIPTION OF THE INVENTION

Illustrative embodiments of the invention are described below. In the interest of clarity, not all features of an actual implementation are described in this specification. It will, of course, be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The present invention relates to a system and method for determining the phase envelope of a gas condensate. A gas condensate is injected into a microchannel. The injection pressure is above the expected dew point of the gas condensate, while the exit pressure is maintained below the expected dew point of the gas condensate. As the gas travels through the microchannel, the local pressure drops to the dew point at some location along the microchannel. Once the pressure crosses the phase boundary, a liquid phase is formed within the microchannel. The liquid is detected as a thin, liquid film that is condensed on the wall of the microchannel. Although the amount of liquid is small, the change in refractive index of the wet surface is substantial. While the scope of the present invention is not so limited, the dew point can be detected accurately for gas condensates as lean as, for example, less than one percent liquid by volume.

For the purposes of this disclosure, a gas condensate is defined as a low density mixture of liquid constituents that are present as gaseous components. One type of gas condensate is defined as a low density mixture of liquid hydrocarbons that are present as gaseous components in a natural gas field. FIG. 1 provides a graphical representation of the phase behavior of one particular, typical, gas condensate. The fluid is in gaseous form above the solid curve and to the right of the critical point, while at least a portion of the fluid is in liquid form once the pressure of the fluid drops below the solid curve. For example, point 101 in FIG. 1 represents the gaseous state of the fluid at a given temperature. As the pressure drops at a constant temperature along the line 103, the fluid crosses the dew point curve, i.e., the solid curve, and a liquid phase forms. Point 105 in FIG. 1 represents a two-phase state of the fluid, exhibiting between 10 and 15 percent liquid by volume. Formation of a liquid constituent within the pores of a gas field formation can severely restrict gas production flow, resulting in reservoir impairment. Accordingly, it is of prime importance to measure the dew points of reservoir gases so that gas production can be operated efficiently.

Figure 2:
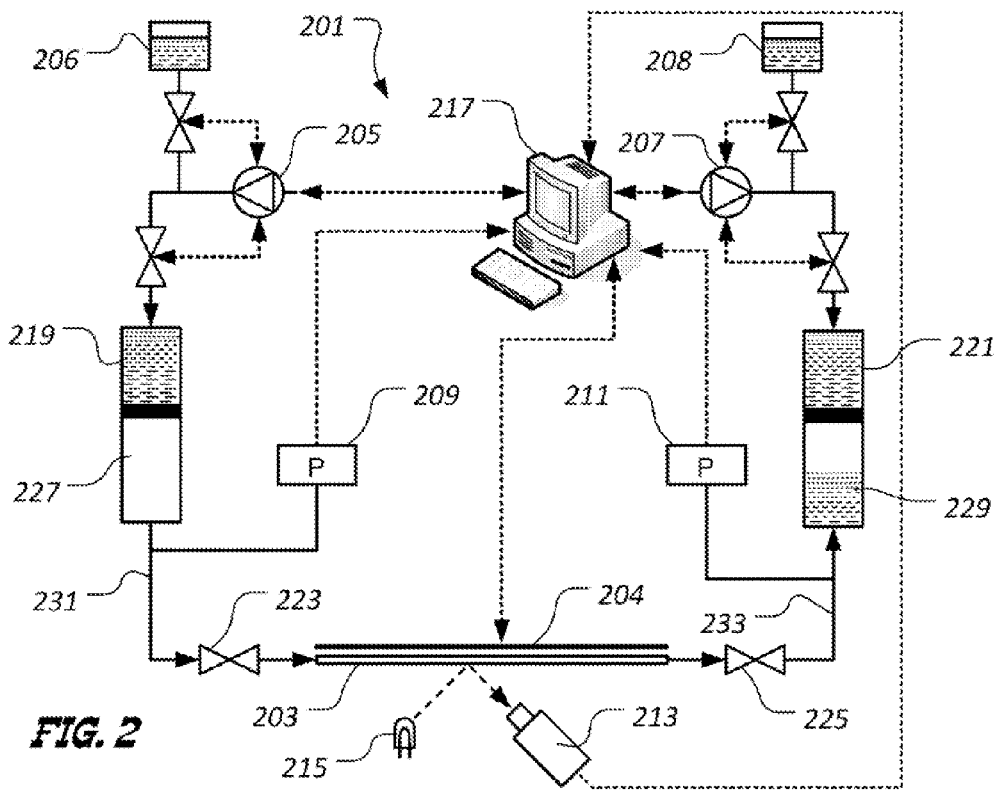
FIG. 2 is a schematic representation of an exemplary system for detecting the phase envelope of a gas condensate.

FIG. 2 provides a schematic representation of an exemplary system 201 for determining the phase envelope of a gas condensate. System 201 comprises a microfluidic device 203, a temperature control device 204, a first pump 205, a second pump 207, an inlet pressure sensor 209, an outlet pressure sensor 211, a camera 213, a light source 215, and a computer 217, an input sample bottle 219, an output sample bottle 221, a sample inlet valve 223, and a sample outlet valve 225. Note that a side, elevational view of microfluidic device 203 is shown in FIG. 2. In one embodiment, temperature control device 204 is a Peltier device, such as those available from Custom Thermoelectric, Inc. of Bishopville, Md., USA. In one embodiment, first and second pumps 205 and 207 are high pressure syringe pumps, such as those available from Teledyne Isco, Inc. of Lincoln, Nebr., USA. Inlet and outlet pressure sensors 209 and 211 are, in one embodiment, pressure sensors such as those available from Sensotreme GmbH of Ramsen, Germany. In one embodiment, camera 213 is a CCD camera, such as those available from Basler AG of Ahrensburg, Germany.

An entrance passageway 301 (shown in FIG. 3) of microfluidic device 203 is in fluid communication via an inlet line 231 with input sample bottle 219. Fluid communication from input sample bottle 219 to microfluidic device 203 is selectively allowed by sample inlet valve 223. An exit passageway 303 (shown in FIG. 3) of microfluidic device 203 is in fluid communication via an outlet line 233 with output sample bottle 221. Fluid communication from microfluidic device 203 to output sample bottle 221 is selectively allowed by sample outlet valve 225. First pump 205 pressurizes input sample bottle 219 with pressurizing fluid from first fluid reservoir 206 to provide a motive force that urges a first portion 227 of a sample fluid, disposed in input sample bottle 219, into microfluidic device 203. Second pump 207 pressurizes a second portion 229 of the sample fluid disposed in output sample bottle 221 with pressurizing fluid from second fluid reservoir 208 to control the pressure in output sample bottle 221 in opposition to a portion of the motive force provided by first pump 205. In other words, first pump 205 and second pump 207 are operated to provide desired absolute pressures and a desired pressure drop between entrance passageway 301 and exit passageway 303 (each shown in FIG. 3) of microfluidic device 203. Temperature control device 204 controls the temperature of the sample fluid in microfluidic device 203.

Still referring to FIG. 2, computer 217 comprises hardware and software that allows computer 217 to receive inputs, such as sensory inputs, image data, and the like; and to control various elements of system 201. Specifically, in the illustrated embodiment, computer 217 receives sensory inputs from inlet pressure sensor 209 and outlet pressure sensor 211. Inlet pressure sensor 209 is in fluid communication with inlet line 231 and senses the pressure of first portion 227 of the sample fluid in inlet line 231. Outlet pressure sensor 211 is in fluid communication with outlet line 233 and senses the pressure of second portion 229 of the sample fluid in outlet line 233. Based on at least the sensory inputs received from inlet pressure sensor 209 and outlet pressure sensor 211, computer 217 controls first pump 205 and second pump 207 to control the pressure drop between entrance passageway 301 and exit passageway 303 (each shown in FIG. 3) of microfluidic device 203. Computer 217 further receives temperature inputs from temperature control device 204 and controls temperature control device 204 based on such inputs. As is discussed in greater detail herein, light source 215 illuminates a substantially transparent, major surface of microfluidic device 203. Light reflected from the substantially transparent major surface of microfluidic device 203 is captured as an image by camera 213. The image is transmitted to computer 217, where it is analyzed.

It should be noted, however, that while the embodiment illustrated in FIG. 2 is controlled by computer 217, the scope of the present invention is not so limited. Rather, elements of system 201 may be controlled by a device other than computer 217. Moreover, system 201, in certain embodiments, may omit computer 217, whereby system 201 is manually controlled by human means.

Figure 3:
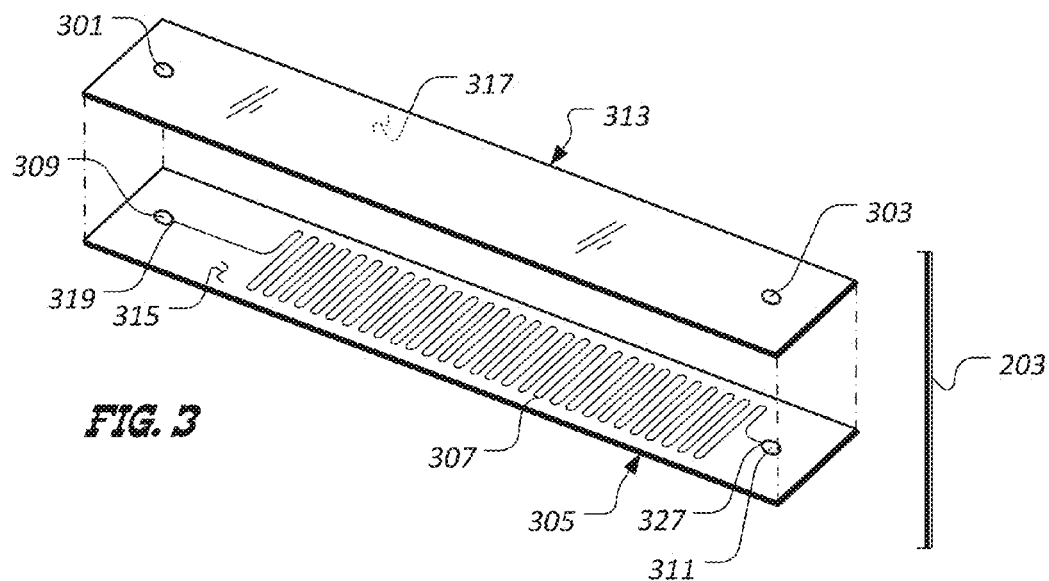
FIG. 3 is an exploded, perspective view of an illustrative embodiment of a microfluidic device.
Figure 4:
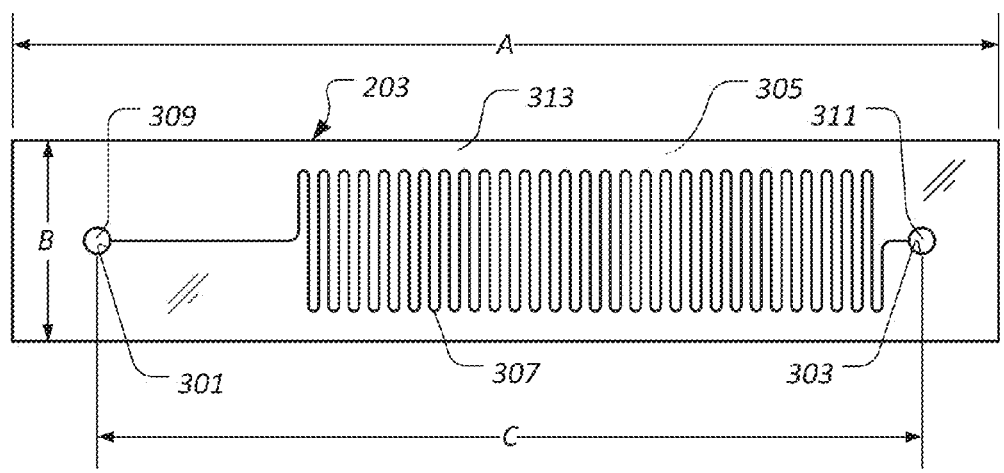
FIG. 4 is a top, plan view of the microfluidic device embodiment of FIG. 3.
Figure 5:
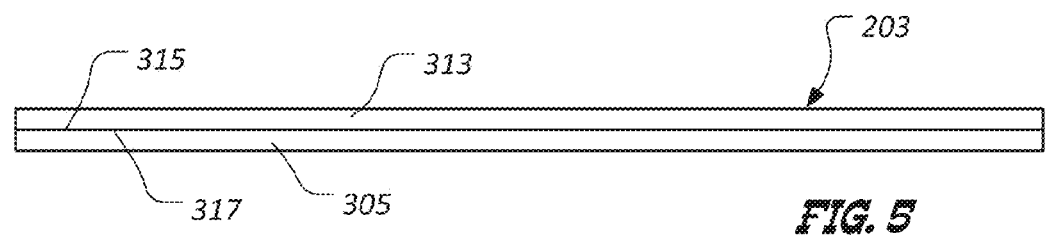
FIG. 5 is a side, elevational view of the microfluidic device embodiment of FIG. 3.

FIGS. 3-5 depict views of an illustrative embodiment of microfluidic device 203. In particular, FIG. 3 depicts an exemplary stylized, exploded, perspective view of microfluidic device 203. FIG. 4 depicts a top, plan view of the embodiment of microfluidic device 203 shown in FIG. 2. FIG. 5 depicts a side, elevational view of the embodiment of microfluidic device 203 shown in FIG. 2. In the illustrated embodiment, microfluidic device 203 comprises a first substrate 305 defining a microchannel 307, an entrance well 309 and an exit well 311. Microchannel 307 extends between and is in fluid communication with entrance well 309 and exit well 311. Microchannel 307 forms a serpentine pattern in first substrate 305, thus allowing microchannel 307 to extend a significant length but occupy a relatively small area. In one embodiment, microchannel 307 exhibits a length of one or more meters, a width of about 100 micrometers, and a depth of about 50 micrometers, although the present invention contemplates other dimensions for microchannel 307. Microfluidic device 203 further comprises a second substrate 313 having a lower surface 317 that is bonded to an upper surface 315 of first substrate 305. When second substrate 313 is bonded to first substrate 305, microchannel 307 is sealed except for an inlet 319 at entrance well 309 and an outlet 327 at exit well 311. Second substrate 313 defines entrance passageway 301 and exit passageway 303 therethrough, which are in fluid communication with entrance well 309 and exit well 311, respectively, of first substrate 305.

In the embodiment depicted in FIG. 3, first substrate 305 is made from silicon, glass, or sapphire, and second substrate 313 is also made from silicon, glass, such as borosilicate glass, or sapphire, although the present invention contemplates other materials. Exemplary borosilicate glasses are manufactured by Schott North America, Inc. of Elmsford, N.Y., USA, and by Corning Incorporated of Corning, N.Y., USA. Microchannel 307, entrance well 309, and exit well 311 are, in one embodiment, first patterned onto first substrate 305 using a photolithography technique and then etched into first substrate 305 using a deep reactive ion etching technique. In one embodiment, entrance passageway 301 and exit passageway 303 are generated in second substrate 313 using a water jet or abrasive drilling technique. First substrate 305 and second substrate 313 are preferably fused to one another using an anodic bonding method after careful cleaning of the bonding surfaces of substrates 305 and 313, e.g., upper surface 315 of first substrate 305 and lower surface 317 of second substrate 313. The present invention contemplates microfluidic device 203 having any suitable size and/or shape needed for a particular implementation. In one embodiment, microfluidic device 203 exhibits an overall length A of about 80 millimeters and an overall width B of about 15 millimeters. In such an embodiment, passageways 301 and 303 are spaced apart a distance C of about 72 millimeters. In an alternative embodiment, microfluidic device 203 may comprise a capillary tube.

Figure 6:
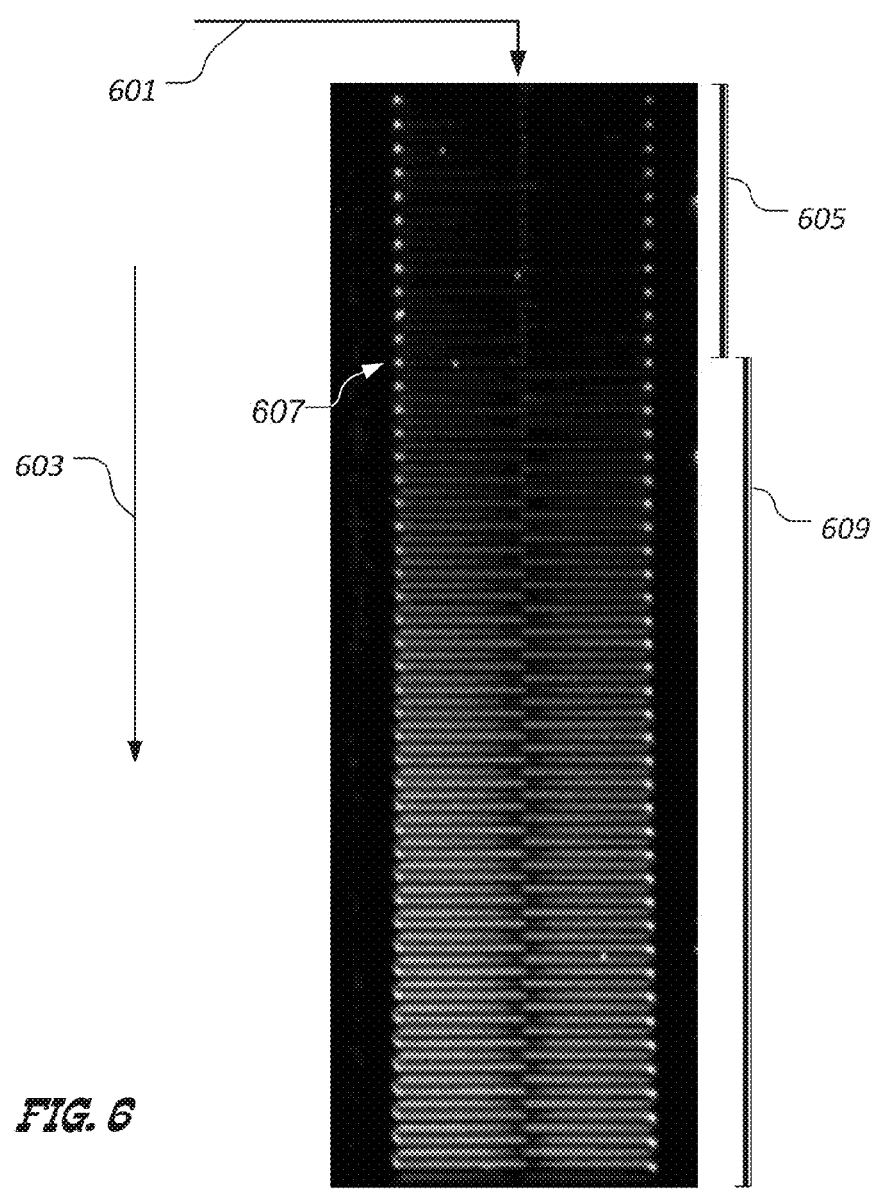
FIG. 6 is a photograph illustrating condensation phenomenon in a top, plan view of an exemplary embodiment of a microfluidic device in use in conjunction with the present invention.

Referring now to FIGS. 2 and 3, a method of determining the phase envelope of a gas condensate comprises injecting the gas condensate into microchannel 307, via entrance passageway 301, at a pressure higher than the dew point of the gas condensate. As the gas condensate flows through microchannel 307, the pressure of the gas condensate drops below the condensation point of the gas condensate. This pressure drop results in a phase change of the gas condensate, i.e., a change from a gaseous state to a two-phase, gaseous and liquid state, within microchannel 307. The liquid portion of the gas condensate when in the two-phase state condenses on a portion of the surfaces of microfluidic device 203 that define microchannel 307. FIG. 6 depicts a photograph of a portion of an exemplary microfluidic device 203, into which a gas condensate has been injected at high pressure, as indicated by arrow 601. The gas condensate is moving in a direction generally corresponding to arrow 603, although in a serpentine fashion, through microchannel 307 and the gas condensate exhibits a progressively lower pressure as it travels through microchannel 307. Within a region 605, the gas condensate is at a pressure above its dew point. Within a region 607, however, the gas condensate exhibits a pressure at or below its dew point. A portion of the gas condensate is condensed on the surfaces of microfluidic device 203 generally within region 607. Microchannel 307 within region 607, in which some portion of the gas condensate has condensed within microchannel 307, appears lighter than the appearance of microchannel 307 within region 605 due to the difference in refractive indices of the gaseous gas condensate/substrate interface and the liquid gas condensate/substrate interface. In the illustrated example, the exemplary gas condensate has a molar composition of about 82 percent $C_1$, about 8.95 percent $C_4$, about 5 percent n-$C_5$, about 1.99 percent n-$C_{10}$, and about 2.01 percent n-$C_{16}$.

Referring again to FIG. 2, the dew point of a fluid at a given temperature is determined by adjusting the pressures exerted onto the gas condensate by first pump 205 and second pump 207 until the gas condensate condenses within microchannel 307. By reducing the pressure differential between first pump 205 and second pump 207 until condensation appears in a portion of microchannel 307, the dew point of the gas condensate, i.e., the pressure at which the gas condensate condenses, can be determined for a given temperature. In one embodiment, system 201 can determine the dew point of a gas condensate within about 10 pounds per square inch. Multiple iterations can be performed to determine the dew point of the gas condensate for multiple corresponding temperatures to determine the phase envelope of the gas condensate. It should be noted that the present method may be performed in certain embodiments by system 201 controlled by computer 217 or the present method may be performed by human means.

Figure 7:
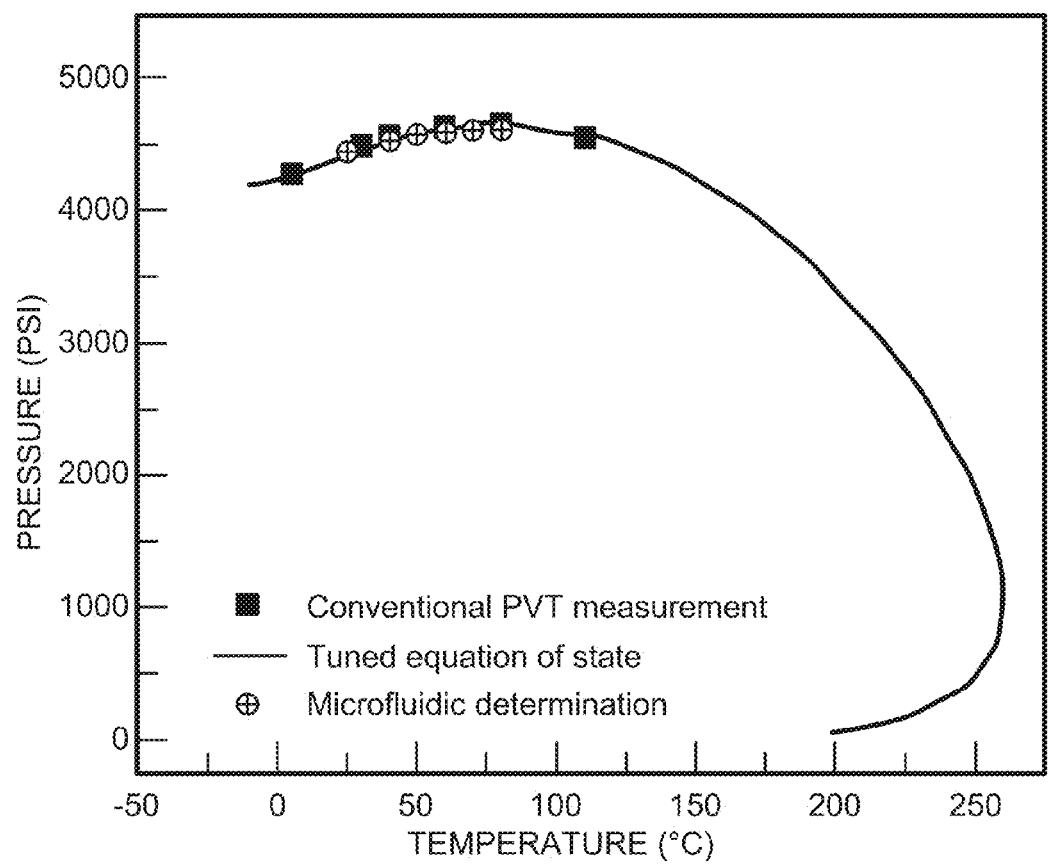
FIG. 7 is a graphical representation of the results of a series of determinations of the dew points of a gas condensate.

FIG. 7 graphically depicts the results of a series of determinations of the dew points of a gas condensate having a molar composition of about 82 percent $C_1$, about 8.95 percent $C_4$, about 5 percent n-$C_5$, about 1.99 percent n-$C_{10}$, and about 2.01 percent n-$C_{16}$ at various temperatures. In FIG. 7, a comparison is made among pressure-volume-temperature (PVT) measurements using conventional PVT cells, a conventional tuned equation of state, and microfluidic determination utilizing the system and/or method of the present invention. Excellent agreement among the determination methods is evident throughout the entire temperature range. The maximum deviation of the dew point pressure determined by the present invention from the conventional determinations in this example is about 30 pounds per square inch, which is within the accuracy of the pressure sensors, such as inlet pressure sensor 209 and outlet pressure sensor 211 of FIG. 2, employed in the system used in the example.

Figure 8:
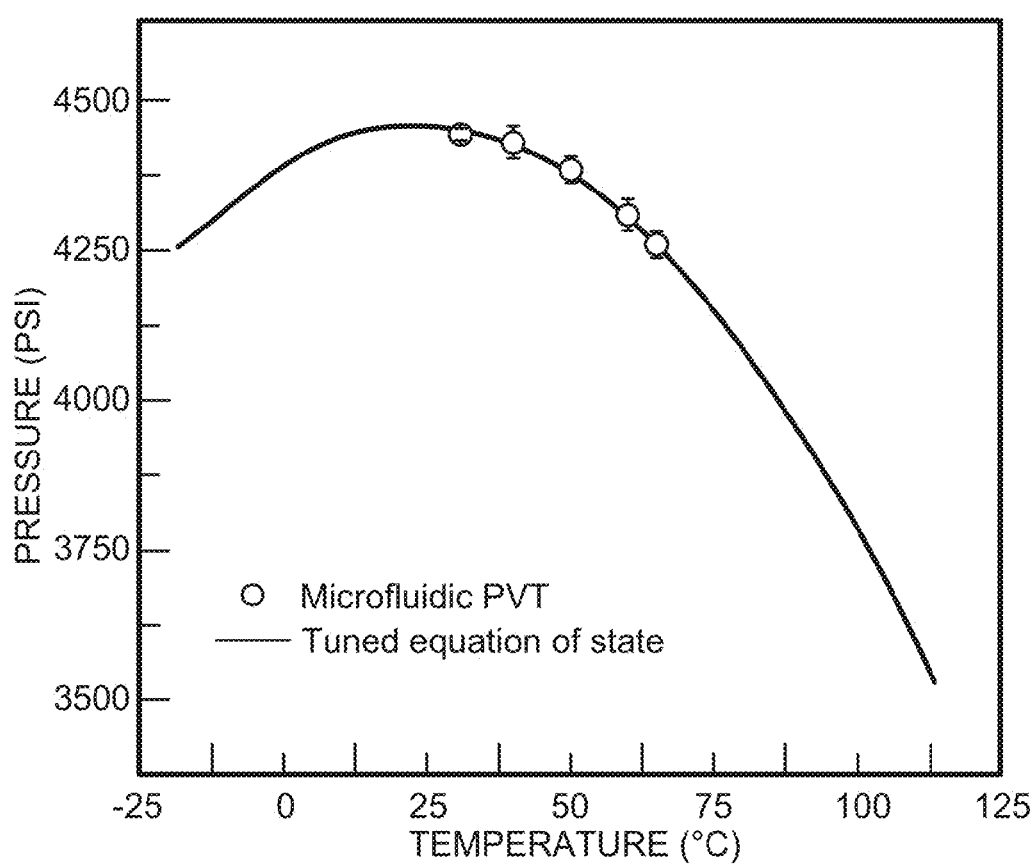
FIG. 8 is a graphical representation of the results of a series of determinations of the dew points of a lean gas condensate.

FIG. 8 graphically depicts the results of a plurality of determinations of the dew points of a lean gas condensate at various temperatures to illustrate the repeatability of the present microfluidic technique. A lean gas condensate is commonly characterized as a gas condensate having only a small amount of liquid dropout, generally less than about one percent by volume. Error bars are shown at each measurement point and show that the standard deviation is less than about eight pounds per square inch in the example.

Dew point measurements using conventional determination means require about one-half day to complete for each temperature of interest. For each series of conventional determinations corresponding to those shown in FIG. 7, at least about three days of testing is required. Conversely, the time required to perform dew point measurements using the present microfluidic technique is less than about one-half hour. This substantial improvement in productivity is due, at least in part, to the short equilibrium time resulting from the relatively small sample volumes utilized by the present microfluidic technique. In addition to the substantial improvement in productivity, the present microfluidic technique is much less labor intensive as compared to conventional techniques. Furthermore, the present microfluidic technique provides improved safety for personnel as compared to conventional techniques when such techniques are used to make determinations of dew points of flammable gas condensates. Conventional techniques require liters of such gas condensates, while the present microfluidic technique requires only a few milliliters of gas condensate. Finally, because of the compactness of the system of the present invention, it can readily be installed in a downhole tool.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below. Although the present invention is shown in a limited number of forms, it is not limited to just these forms, but is amenable to various changes and modifications.

What is claimed is:

1. A system for determining the phase envelope of a gas condensate, comprising:
    a microfluidic device defining an entrance passageway, an exit passageway, and a microchannel in fluid communication with the entrance passageway and the exit passageway;
    an input sample bottle in fluid communication with the entrance of the microfluidic device;
    a first pump operably associated with the input sample bottle for urging the gas condensate, disposed in the input sample bottle, into the entrance of the microfluidic device;
    an output sample bottle in fluid communication with the exit passageway of the microfluidic device;
    a second pump operably associated with the output sample bottle for pressurizing the gas condensate, disposed in the output sample bottle, in opposition to the first pump; and
    a temperature control device for controlling the temperature of the gas condensate in the microchannel,
    wherein the first pump and the second pump are operable to provide a desired pressure drop across the microchannel of the microfluidic device.

2. The system of claim 1, wherein the microfluidic device comprises:
    a first substrate defining the microchannel, an entrance well, and an exit well, the microchannel extending between and in fluid communication with the entrance well and the exit well; and
    a second substrate attached to the first substrate to form the microfluidic device, the second substrate defining the entrance passageway in fluid communication with the entrance well and the exit passageway in fluid communication with the exit well.

3. The system of claim wherein the microchannel exhibits a serpentine shape.

4. The system of claim 1, wherein the microfluidic device comprises a capillary tube.

5. The system of claim 1, further comprising:
    an net pressure sensor configured to measure the pressure of the gas condensate urged into the entrance passageway of the microfluidic device; and
    an outlet pressure sensor configured to measure the pressure of the gas condensate in the exit passageway of the microfluidic device.

6. The system of claim 1, further comprising a computer for operating the first pump and the second pump based at least upon the pressure of the gas condensate urged into the entrance passageway of the microfluidic device and the pressure of the gas condensate in the exit passageway of the microfluidic device.

7. The system of claim 6, wherein the computer operates he temperature control device, 8. The system of claim 1, further comprising a camera operably associated with the microfluidic device.

9. The system of claim 1, further comprising:
    an inlet valve in fluid communication with the input sample bottle and the entrance passageway of the microfluidic device; and
    an outlet valve in fluid communication with the output sample bottle and the exit passageway of the microfluidic device.

10. The system of claim 1, wherein the system is installed in a downhole tool.

11. A system for determining the phase envelope of a gas condensate, comprising:
    a microfluidic device defining an entrance passageway, an exit passageway, and a microchannel in fluid communication with the entrance passageway and the exit passageway;
    an input sample bottle in fluid communication with the entrance of the microfluidic device;
    a first pump operably associated with the input sample bottle for urging the gas condensate, disposed in the input sample bottle, into the entrance of the microfluidic device;
    an inlet pressure sensor operably associated with the entrance passageway of the microfluidic device;
    an output sample bottle in fluid communication with the exit of the microfluidic device;
    a second pump operably associated with the output sample bottle for pressurizing the gas condensate, disposed in the output sample bottle, in opposition to the first pump;
    an outlet pressure sensor operably associated with the exit passageway of the microfluidic device;
    a temperature control device for controlling the temperature of the gas condensate in the microchannel;
    a camera operably associated with the microfluidic device; and
    a computer operably associated with the first pump, the inlet pressure sensor, the second pump, and the outlet pressure sensor for operating the first pump and the second pump to provide a desired pressure drop across the microchannel of the microfluidic device.

12. The system of claim 11, wherein the computer is operably associated with the camera for analyzing images of the microfluidic device.

13. The system of claim 11, wherein the computer is operably associated with the temperature control device for controlling the temperature of the gas condensate in the microchannel.

14. The system of claim 11, further comprising a light source for illuminating the microfluidic device.

15. The system of claim 11, wherein the microfluidic device cornprises:
    a first substrate defining the microchannel, an entrance well, and an exit well, the microchannel extending between and in fluid communication with the entrance well and the exit well; and
    a second substrate attached to the first substrate to form the microfluidic device, the second substrate defining the entrance passageway in fluid communication with the entrance well and the exit passageway in fluid communication with the exit well.

16. The system of claim 11, wherein the microfluidic device comprises a capillary tube.

17. The system of claim 11 further comprising:
- an inlet valve in fluid communication with the input sample bottle and the entrance passageway of the microfluidic device; and
- an outlet valve in fluid communication with the output sample bottle and the exit passageway of the microfluidic device.

18. The system of claim 11, wherein the system is installed in a downhole tool.

19. A method for determining the phase envelope of a gas condensate, comprising:
- injecting a gas condensate into a microchannel of a microfluidic device at a pressure above an expected dew point of the gas condensate; and
- monitoring the gas condensate in the microchannel for an indication of a phase change of the gas condensate by producing an image of the gas condensate in the microchannel and analyzing the image with a computer.

20. The method of claim 19, wherein injecting the gas condensate into the microchannel of the microfluidic device is accomplished by:
- operating a first pump to urge a first portion of the gas condensate into an entrance passageway of the microfluidic device; and
- operating a second pump to pressurize a second portion of the gas condensate in an exit passageway of the microfluidic device in opposition to the first pump.

21. The method of claim 20, wherein operating the first pump and operating the second pump are accomplished by a computer.

22. The method of claim 20, wherein operating the first pump and operating the second pump are further accomplished by monitoring the pressure of the gas condensate at the entrance passageway of the microfluidic device and by monitoring the pressure of the gas condensate at the exit passageway of the microfluidic device.

23. The method of claim 19, further comprising illuminating the microfluidic device.

24. The method of claim 19, further comprising varying the temperature of the gas condensate in the microchannel.

* * * * *